US009138130B2

(12) United States Patent
Nakamura et al.

(10) Patent No.: US 9,138,130 B2
(45) Date of Patent: Sep. 22, 2015

(54) ASSIST ASSEMBLY FOR PROPULSION OF ENDOSCOPE

(71) Applicant: FUJIFILM CORPORATION, Tokyo (JP)

(72) Inventors: Takayuki Nakamura, Ashigarakami-gun (JP); Tsuyoshi Ashida, Ashigarakami-gun (JP); Yasunori Ohta, Ashigarakami-gun (JP); Shinichi Yamakawa, Ashigarakami-gun (JP); Charles Alan Brantingham, St. Paul, MN (US)

(73) Assignee: FUJIFILM Corporation, Tokyo (JP)

( * ) Notice: Subject to any disclaimer, the term of this patent is extended or adjusted under 35 U.S.C. 154(b) by 150 days.

(21) Appl. No.: 13/936,698

(22) Filed: Jul. 8, 2013

(65) Prior Publication Data

US 2014/0107419 A1    Apr. 17, 2014

Related U.S. Application Data

(60) Provisional application No. 61/669,276, filed on Jul. 9, 2012.

(51) Int. Cl.
*A61B 1/00* (2006.01)
(52) U.S. Cl.
CPC ........... *A61B 1/0016* (2013.01); *A61B 1/00135* (2013.01)
(58) Field of Classification Search
USPC ........................................................ 600/114
See application file for complete search history.

(56) References Cited

U.S. PATENT DOCUMENTS

| 4,558,971 A | * | 12/1985 | David .......................... 405/158 |
| 7,736,300 B2 | * | 6/2010 | Ziegler et al. ................. 600/114 |
| 8,795,158 B2 | * | 8/2014 | Yamakawa et al. ........... 600/114 |
| 2005/0272976 A1 | | 12/2005 | Tanaka et al. |
| 2006/0089533 A1 | | 4/2006 | Ziegler et al. |

FOREIGN PATENT DOCUMENTS

| JP | 1-227737 A | 9/1989 |
| JP | 8-155168 A | 6/1996 |

(Continued)

OTHER PUBLICATIONS

Written Opinion of the International Searching Authority, dated Feb. 21, 2012, issued in PCT/JP2012/051225.

*Primary Examiner* — Matthew J Kasztejna
(74) *Attorney, Agent, or Firm* — Birch, Stewart, Kolasch & Birch, LLP

(57) ABSTRACT

An assist assembly for propulsion of a tip device of an endoscope in a body cavity includes an attachment sleeve and a support sleeve. A deformable circulation device is disposed to extend over inner and outer surfaces of the support sleeve, for endlessly moving in an axial direction of the tip device. Plural rollers are disposed on the support sleeve in a rotatable manner, for pressing an inner surface of the circulation device. An alignment projection is formed on the inner surface of the circulation device to project at a height L1. A location offset prevention groove is formed in the rollers at a depth L2, for receiving the alignment projection, and satisfying a condition $L1 \geq L2$, to prevent location offset of the circulation device from the rollers. Drive wheels tension the circulation device in cooperation with the rollers by deforming the alignment projection in the location offset prevention groove.

11 Claims, 9 Drawing Sheets

(56) References Cited

FOREIGN PATENT DOCUMENTS

| | | | |
|---|---|---|---|
| JP | 10-273075 A | 10/1998 |
| JP | 2000-168645 A | 6/2000 |
| JP | 2005-253892 A | 9/2005 |
| JP | 2009-513250 A | 4/2009 |

* cited by examiner

ASSIST ASSEMBLY FOR PROPULSION OF ENDOSCOPE

CROSS REFERENCE TO RELATED APPLICATIONS

This Non-Provisional application claims the benefit of U.S. Provisional Application No. 61/669,276 filed on Jul. 9, 2012. The entire contents of the above application are hereby incorporated by reference.

BACKGROUND OF THE INVENTION

1. Field of the Invention

The present invention relates to an assist assembly for propulsion of a tip device of an endoscope into a body.

2. Description Related to the Prior Art

In medical and industrial fields, an endoscope is widely used for imaging of a body. The endoscope has a handle and an elongated tube for entry in the body. A tip device of the elongated tube contains an imaging unit such as a CCD. An image created by the imaging unit is displayed on a monitor.

Various forms of assist assembly for the endoscope have been suggested for assisting the entry of the endoscope in view of difficulty in the entry of the endoscope. For example, U.S. Ser. No. 2005/272,976 (corresponding to JP-A2005-253892) discloses the assist assembly for the endoscope (referred to as a propulsion device for an endoscope according to the publication) including a tubular support and a circulation device (endless track device), the support being mounted on the tip device of the elongated tube of the endoscope, the circulation device being secured to the support movably in circulation. The circulation device mentioned above moves endlessly in a state of contact of its outer surface with a tissue wall of the body, for example, a gastrointestinal tract of a human body, and thus applies force of propulsion to the tip device. Accordingly, it is possible easily to enter the endoscope even in the gastrointestinal tract of a very tortuous form, for example, a large intestine.

In the assist assembly for the endoscope mentioned above, a motor rotates a wire. A magnetic bar secured to an end of the wire is rotated to move the circulation device in circulation, the circulation device being extended in contact with magnetic rollers. The magnetic bar is in a form in which N and S poles are wound alternately and helically, and operates as a worm gear. Also, the rollers have N and S poles arranged alternately on its outer surface, and operate as worm wheels. The circulation device moves in the circulation in a state of contact with the tissue wall of the gastrointestinal tract, and constantly receives pressure from the tissue wall. The circulation device is likely to offset on the rollers. Upon occurrence of the offset, the circulation device may slip to drop driving force of the circulation device, which may become unable to assist the entry of the endoscope.

SUMMARY OF THE INVENTION

In view of the foregoing problems, an object of the present invention is to provide an assist assembly for propulsion of a tip device of an endoscope into a body, and in which drop in driving force of a circulation device can be prevented.

In order to achieve the above and other objects and advantages of this invention, an assist assembly for propulsion of a tip device of an endoscope in a body cavity includes an attachment sleeve for mounting on the tip device. A support sleeve is disposed around the attachment sleeve. A deformable circulation device is disposed to extend over inner and outer surfaces of the support sleeve, for contacting a wall of the body cavity, and endlessly moving in an axial direction of the tip device. Plural rollers are disposed on the support sleeve in a rotatable manner, for pressing an inner surface of the circulation device. A projection is formed on the inner surface of the circulation device to project at a height $L1$. A location offset prevention groove is formed in the rollers at a depth $L2$, for receiving the projection, and satisfying a condition $L1 \geq L2$, to prevent location offset of the circulation device from the rollers. A drive mechanism tensions the circulation device in cooperation with the rollers by deforming the projection in the location offset prevention groove and by pressing the inner surface of the circulation device on the rollers, endlessly to drive the circulation device by rotating.

The projection continuously extends in the axial direction on the circulation device.

Furthermore, an insertion groove is formed in the support sleeve, for receiving insertion of the projection.

The plural rollers are arranged in the axial direction.

The rollers are first to Nth rollers arranged on the support sleeve at a predetermined pitch in a circumferential direction defined around the axial direction. The projection is first to Nth projections arranged on the circulation device to correspond to respectively the first to Nth rollers.

The drive mechanism includes a drive sleeve disposed between the attachment sleeve and the support sleeve. A worm gear is formed on an outer surface of the drive sleeve, for moving the circulation device.

The drive mechanism includes a plurality of rotatable drive wheels, engaged with the worm gear and the circulation device, for moving the circulation device upon rotation of the worm gear.

The circulation device covers the support sleeve in an entire manner in a bag shape.

In another preferred embodiment, the circulation device includes plural endless belts for partially covering the support sleeve in a circumferential direction.

According to the present invention, the projection formed on the circulation device is received in the location offset prevention groove formed in the rollers, so that occurrence of location offset of the circulation device can be prevented to prevent drop in the driving force of the circulation device. Also, the projection is deformed by pressure on a groove bottom surface in the location offset prevention groove. An inner surface of the circulation device of the portion without the projection is pressed on an outer surface of the rollers. Thus, high driving force can be obtained, as pressure of contact between the projection and the rollers and pressure of contact between the rollers and the portion of the circulation device without the projection are higher than a structure without contact of the projection with the groove bottom surface of the location offset prevention groove and than a structure without contact of the inner surface of the circulation device with the rollers. Therefore, it is possible stably to assist the entry of the endoscope in the present invention.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
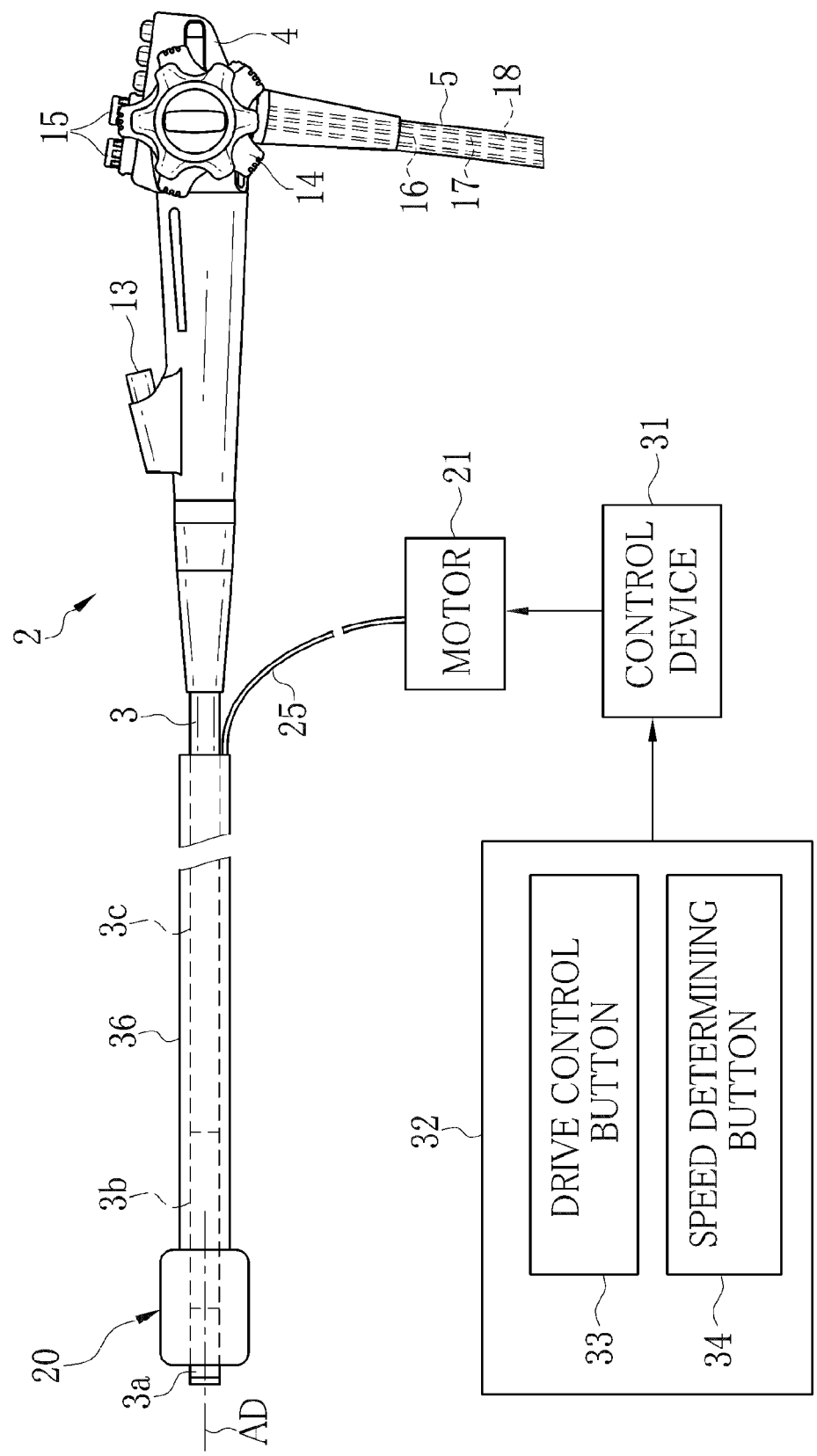
FIG. 1 is an explanatory view illustrating an endoscope on which an assist assembly is mounted.
Figure 2:
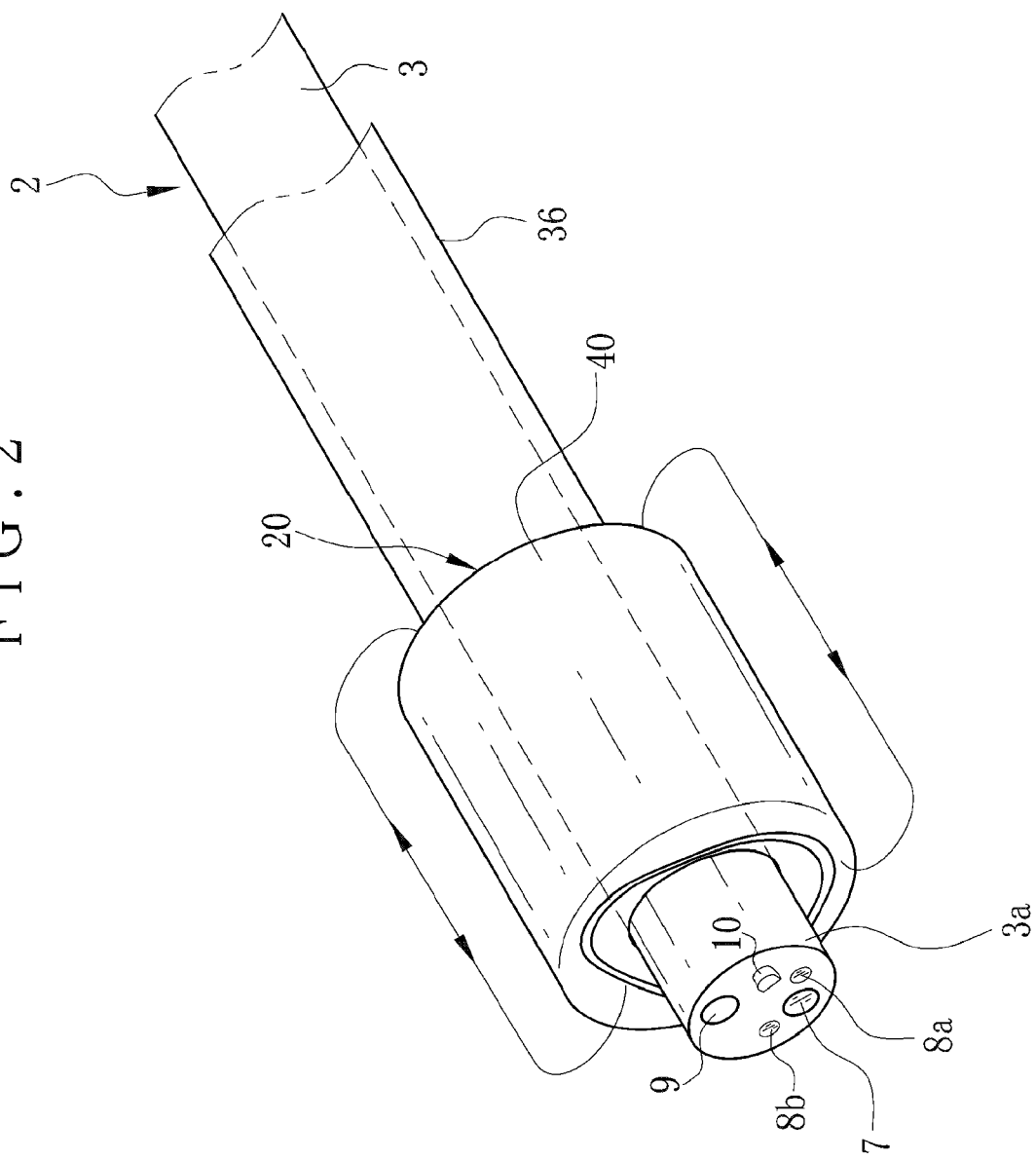
FIG. 2 is a perspective view illustrating a state of mounting the assist assembly on a tip device of the endoscope.

As illustrated in FIGS. 1 and 2, a medical endoscope 2 is constituted by an elongated tube 3, a handle 4, and a universal cord 5, the elongated tube 3 being entered in a body cavity, for example, gastrointestinal tract, such as a large intestine, the handle 4 being used for holding the endoscope 2 and manipulating the elongated tube 3, the universal cord 5 connecting the endoscope 2 to a processing apparatus, light source apparatus, and air/water supply apparatus (all not shown).

The elongated tube 3 includes a rigid tip device 3a, a steering device 3b and a flexible portion 3c. A solid state imaging element is incorporated in the tip device 3a, for example, CCD image sensor. The steering device 3b is disposed on a proximal side of the tip device 3a, and bendable up and down and to the right and left. The flexible portion 3c is disposed between the steering device 3b and the handle 4.

The tip device 3a of the elongated tube 3 has a viewing window 7, lighting windows 8a and 8b, and a forceps outlet 9 for protruding a tip of a forceps. An ejection nozzle 10 is formed in the tip device 3a for ejecting air or washing water to the viewing window 7.

The lighting windows 8a and 8b are disposed on the sides of the viewing window 7. The lighting windows 8a and 8b emit light for illumination from a light source apparatus to an object of imaging in a gastrointestinal tract. Reflected light of the light for illumination from the object of imaging passes through the viewing window 7, and becomes incident upon a CCD sensor disposed behind the same.

A forceps inlet 13 is formed in the handle 4. A forceps channel extends through the elongated tube 3 from the forceps outlet 9 toward the forceps inlet 13. Various medical instruments, such as forceps, injection needle, high frequency scalpel or the like, are entered in the forceps inlet 13 for diagnosis or treatment.

The handle 4 has angle adjusting knobs 14 for steering and a fluid button 15, the angle adjusting knobs 14 bending the steering device 3b up and down and to the right and left, the fluid button 15 being used for supply and suction of air and water among various operations.

The universal cord 5 is coupled to the handle 4. An air/water supply tube 16, a signal cable 17 and a light guide device 18 are stored in the universal cord 5. A proximal end of the air/water supply tube 16 is connected with the air/water supply apparatus. A distal end of the air/water supply tube 16 is connected with the ejection nozzle 10. The air/water supply tube 16 sends air or washing water supplied by the air/water supply apparatus to the ejection nozzle 10. A proximal end of the signal cable 17 is connected with the processing apparatus. A distal end of the signal cable 17 is connected with the CCD image sensor, so that the signal cable 17 transmits a control signal and image signal. A distal end of the light guide device 18 is connected with the lighting windows 8a and 8b. A proximal end of the light guide device 18 is connected with the light source apparatus, so that the light guide device 18 transmits light for illumination from the light source apparatus to the lighting windows 8a and 8b.

An assist assembly 20 is secured to the tip device 3a removably, for moving the elongated tube 3 back or forth in a gastrointestinal tract. The assist assembly 20 is driven by a motor 21. The motor 21 is connected with a torque wire 22 (See FIG. 4) for transmitting rotational torque to propel the assist assembly 20. The torque wire 22 is inserted through a flexible protection sheath 25 of a tubular form in a rotatable manner.

A control device 31 controls the motor 21. The control device 31 is connected to an input interface 32. The input interface 32 includes a drive control button 33 and a speed determining button 34. The drive control button 33 is for inputting a command signal of advance, return and stop of the assist assembly 20. The speed determining button 34 is for determining a moving speed.

An elastic overtube 36, for example, formed from rubber, is mounted on the outside of the elongated tube 3. The overtube 36 is so disposed as to keep a small clearance space between the same and the elongated tube 3. A tip of the overtube 36 is connected to the assist assembly 20. Also, the protection sheath 25 is inserted through the overtube 36.

The assist assembly 20 includes a circulation device for contacting a tissue wall of the gastrointestinal tract to generate force for propulsion or return for the elongated tube 3 of the endoscope 2. In the present embodiment, a circulation device 40 (endless track device), for example, referred to as a toroid, moves endlessly in an axial direction AD.

Figure 3:
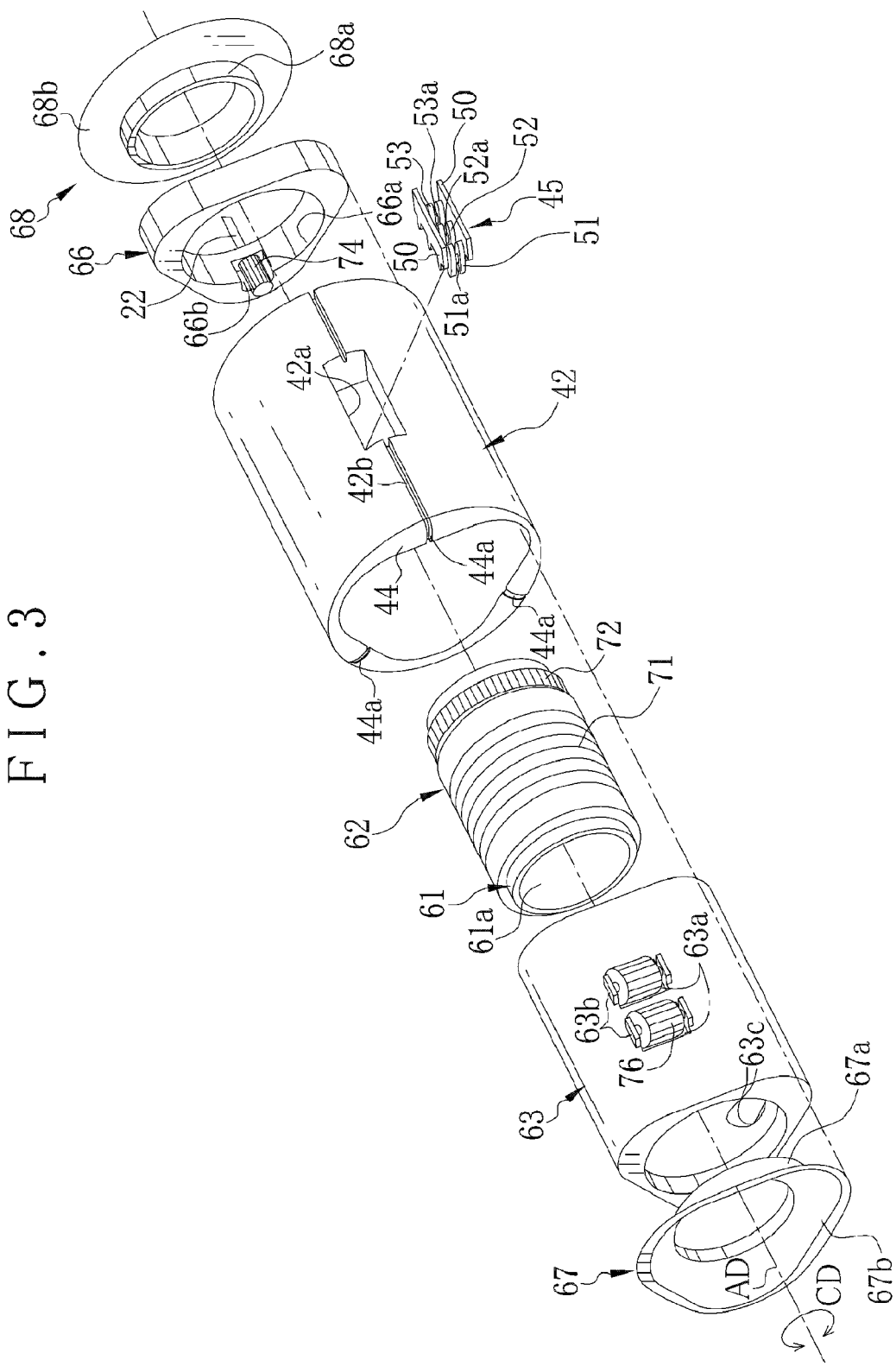
FIG. 3 is an exploded perspective view illustrating main portions of the assist assembly.
Figure 4:
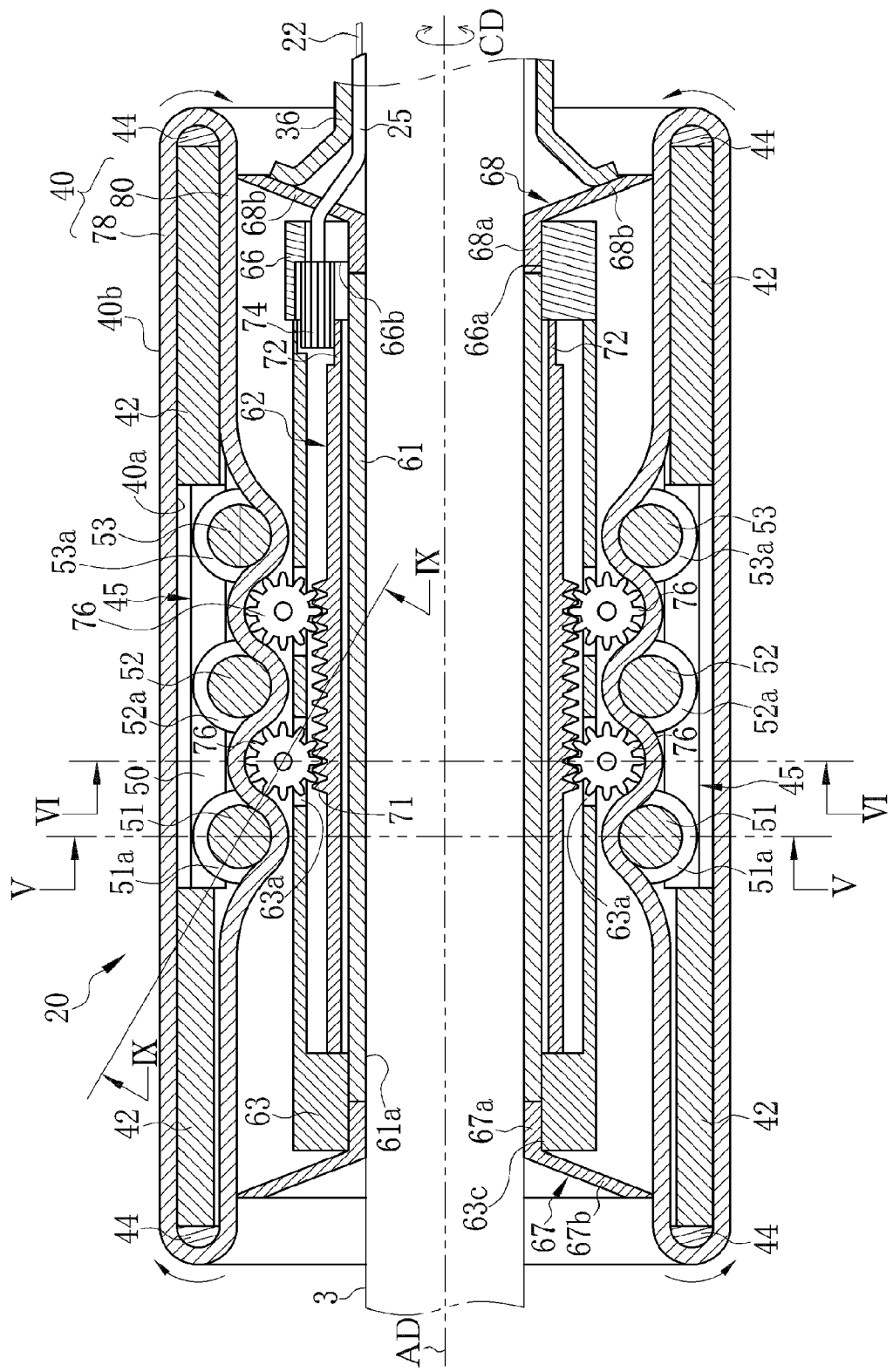
FIG. 4 is a section illustrating the assist assembly.
Figure 5:
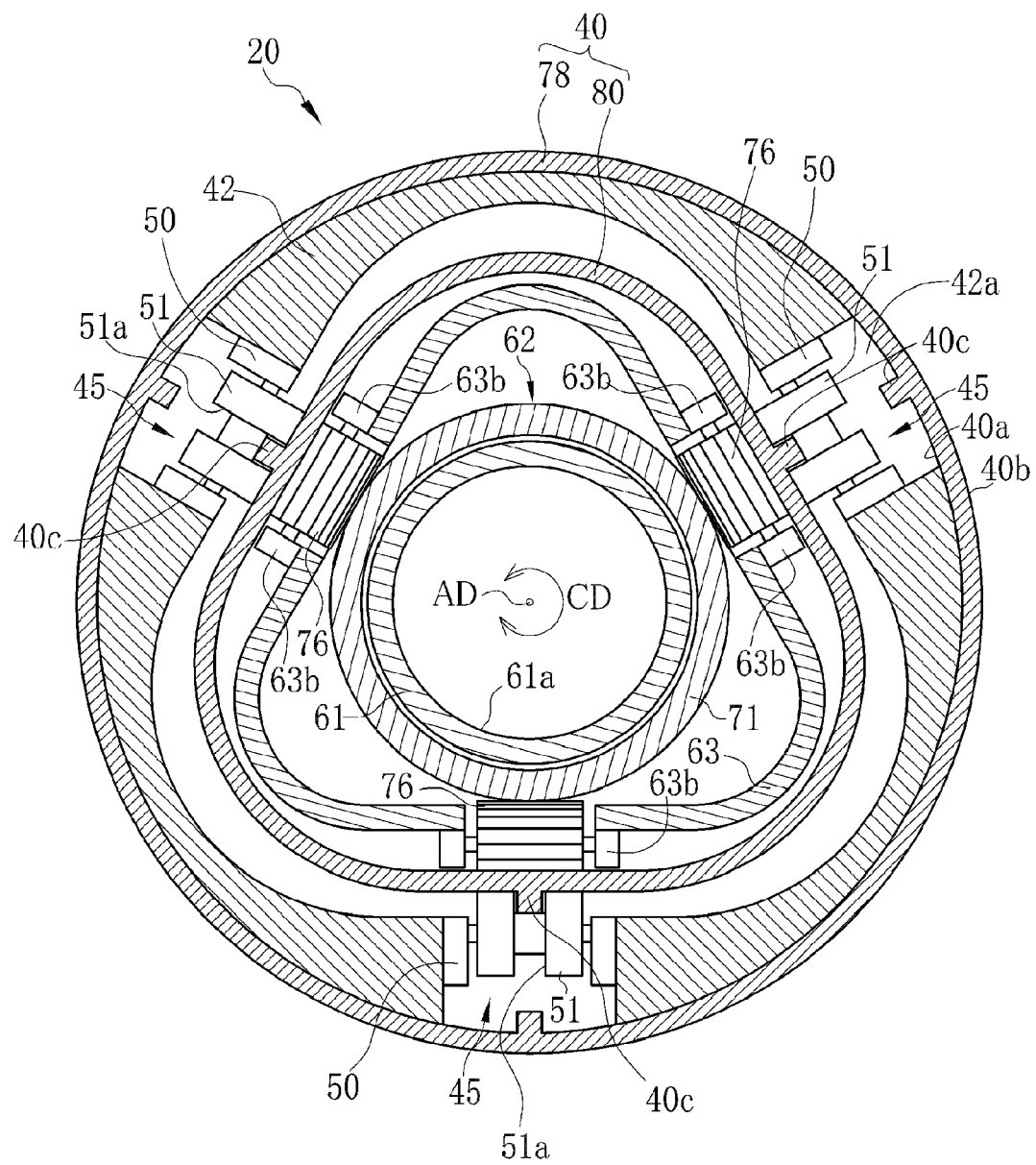
FIG. 5 is a section illustrating the assist assembly on line V-V in FIG. 4.
Figure 6:
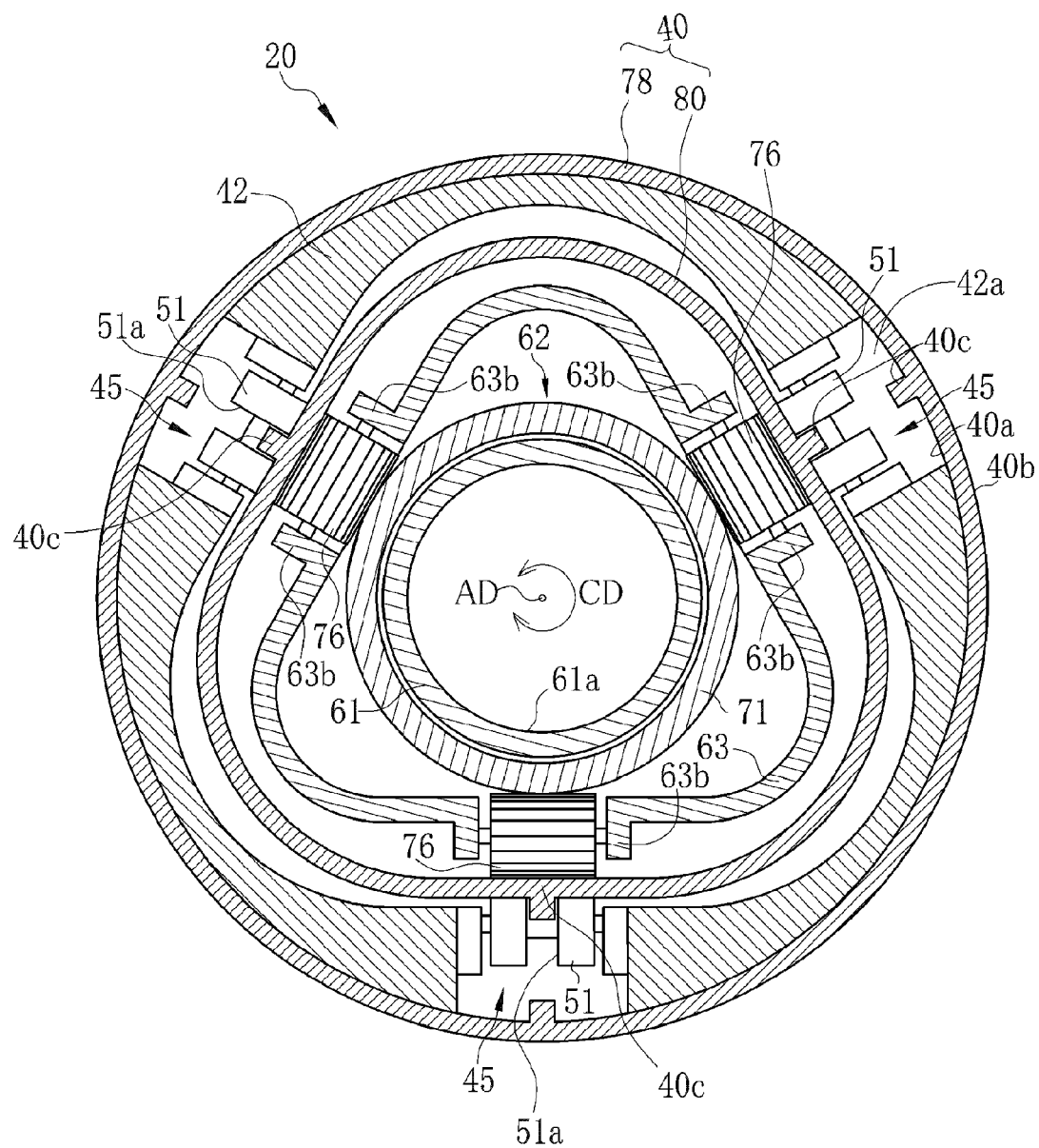
FIG. 6 is a section illustrating the assist assembly on line VI-VI in FIG. 4.

As illustrated in FIGS. 4-6, the circulation device 40 covers the entirety of a circumference of a support sleeve 42 (barrel sleeve) in a state supported by the support sleeve 42. The circulation device 40 moves in its axial direction in circulation. In FIG. 3, the circulation device 40 is not shown. For the circulation device 40, resiliently deformable material with flexibility and expandability is used, for example, biocompatible plastics, such as polyvinyl chloride, polyamide resin, fluorocarbon resin, urethane and polyurethane.

A shape of the support sleeve 42 as viewed in a cross section perpendicular to the axial direction AD is circular with respect to an outer surface, and is substantially triangular in a rounded form by curving vertices of a regular triangle, with respect to an inner surface. To mount the circulation device 40 on the support sleeve 42, at first a sheet of resin shaped in a tubular form is entered in the support sleeve 42. Then front and rear ends of the tubular sheet is bent back externally, and are attached to one another by thermal welding or the like. Thus, the circulation device 40 is formed in a bag shape in which a doughnut form is extended along the hole. Note that the circulation device 40 may be formed by molding by use of molds.

Annular guides 44 are attached to proximal and distal ends of the support sleeve 42 for contacting the bent portions of the circulation device 40. The guides 44 are formed from material, such as resin, for enabling the circulation device 40 to move smoothly in circulation (for example, nylon). It is noted that the guides 44 may be formed from a material other than nylon with easy slip, such as PEEK, Teflon (registered trademark) and the like.

Three flat portions are disposed on the inner surface of the support sleeve 42. Openings 42a are formed in respectively the flat portions. Roller units 45 are secured inside respectively the openings 42a, for pressing the circulation device 40 toward drive wheels 76 (worm wheels). The roller units 45 have two support plates 50. First to third rollers 51-53 are supported in a rotatable manner between the support plates 50, and arranged in the axial direction AD. Portions of the circulation device 40 for contacting the first to third rollers 51-53 have a larger thickness than its remaining portions, and higher rigidity than the remaining portions. It is noted that the first to third rollers 51-53 may be secured directly to the support sleeve 42 without use of the support plates 50.

Figure 7:
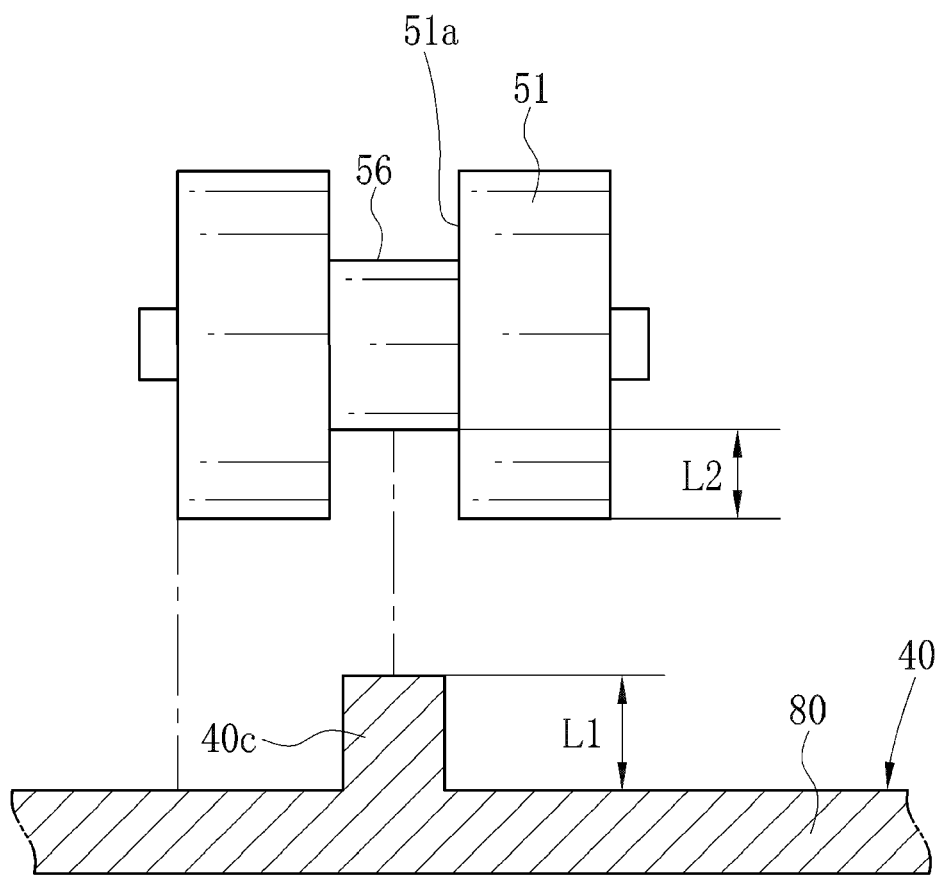
FIG. 7 is a section in enlargement illustrating a circulation device and rollers.

As illustrated in FIG. 7, location offset prevention grooves 51a-53a (roller grooves) are formed in the center of respectively the first to third rollers 51-53. Furthermore, an inner surface 40a of the circulation device 40 is provided with three alignment projections 40c (ridges) corresponding to the three units 45. The alignment projections 40c are formed to extend in the entire circumference of the circulation device 40 in its turning direction (circulating direction), are received in the location offset prevention grooves 51a-53a, and prevent the circulation device 40 from offsetting in a circumferential direction CD (transverse direction) during the turn. Also, insertion grooves 42b (track grooves) are formed in the support sleeve 42 for receiving the alignment projections 40c. Insertion grooves 44a (track grooves) are formed in the guides 44, too.

Let L1 be an initial height of the alignment projections 40c. Let L2 be a depth of the location offset prevention grooves 51a, 52a and 53a. The depth L2 of the location offset prevention grooves 51a-53a is smaller than the height L1 of the alignment projections 40c, to satisfy a condition L1>L2. In contrast, a depth of the insertion grooves 42b and 44a formed in the support sleeve 42 and the guides 44 is larger than the height L1 of the alignment projections 40c. It is noted that a smoothing agent can be applied between the alignment projections 40c and the insertion grooves 42b and 44a or the location offset prevention grooves 51a-53a, to facilitate slip.

In the support sleeve 42, an attachment sleeve 61 (shaft sleeve), a rotatable drive sleeve 62 and a container sleeve 63 (support) are disposed. The attachment sleeve 61 is mounted on the tip device 3a of the endoscope 2. The drive sleeve 62 is disposed outside the attachment sleeve 61. The container sleeve 63 contains the attachment sleeve 61 and the drive sleeve 62.

A support frame 66 (lid) is attached to a proximal end of the container sleeve 63. A distal guide ring 67 is attached to a distal end of the container sleeve 63 for preventing entry of a tissue wall of the gastrointestinal tract. Similarly, a proximal guide ring 68 is attached to the support frame 66.

The drive sleeve 62 is mounted externally on the attachment sleeve 61, and rotatable about the axial direction AD. Teeth of a worm gear 71 and a spur gear 72 are formed on the drive sleeve 62. The spur gear 72 is formed at a proximal end of the drive sleeve 62, and meshed with an input gear 74. Rotation of the motor 21 is transmitted to the input gear 74 by the torque wire 22. When the spur gear 72 is rotated by the input gear 74, the drive sleeve 62 rotates.

The container sleeve 63 is in a substantially triangular shape of a rounded form by curving vertices of a regular triangle for correspondence with an inner surface of the support sleeve 42, and is disposed by aligning its center substantially with a center of the support sleeve 42. Openings 63a are formed in respectively flat portions or three portions of the container sleeve 63. Two of the drive wheels 76 as a drive mechanism are disposed in each of the three openings 63a. Securing ribs 63b are formed on the container sleeve 63, for supporting the drive wheels 76 in a rotatable manner. The drive wheels 76 are disposed between the first roller 51 and the second roller 52 and between the second roller 52 and the third roller 53.

The drive wheels 76 or worm wheels are meshed with the worm gear 71 of the drive sleeve 62, contact an outer surface 40b of the circulation device 40, and support the circulation device 40 between the same and the first to third rollers 51-53. Each of the drive wheels 76 is overlapped with respectively the first to third rollers 51-53 in a radial direction of the support sleeve 42, to apply tension to the circulation device 40 in a curved shape between the first to third rollers 51-53 and the drive wheels 76. It is noted that, in FIG. 4, teeth of the drive wheels 76 are depicted with a large height, but actually have such a small height that the circulation device 40 can be free from damage.

Figure 8:
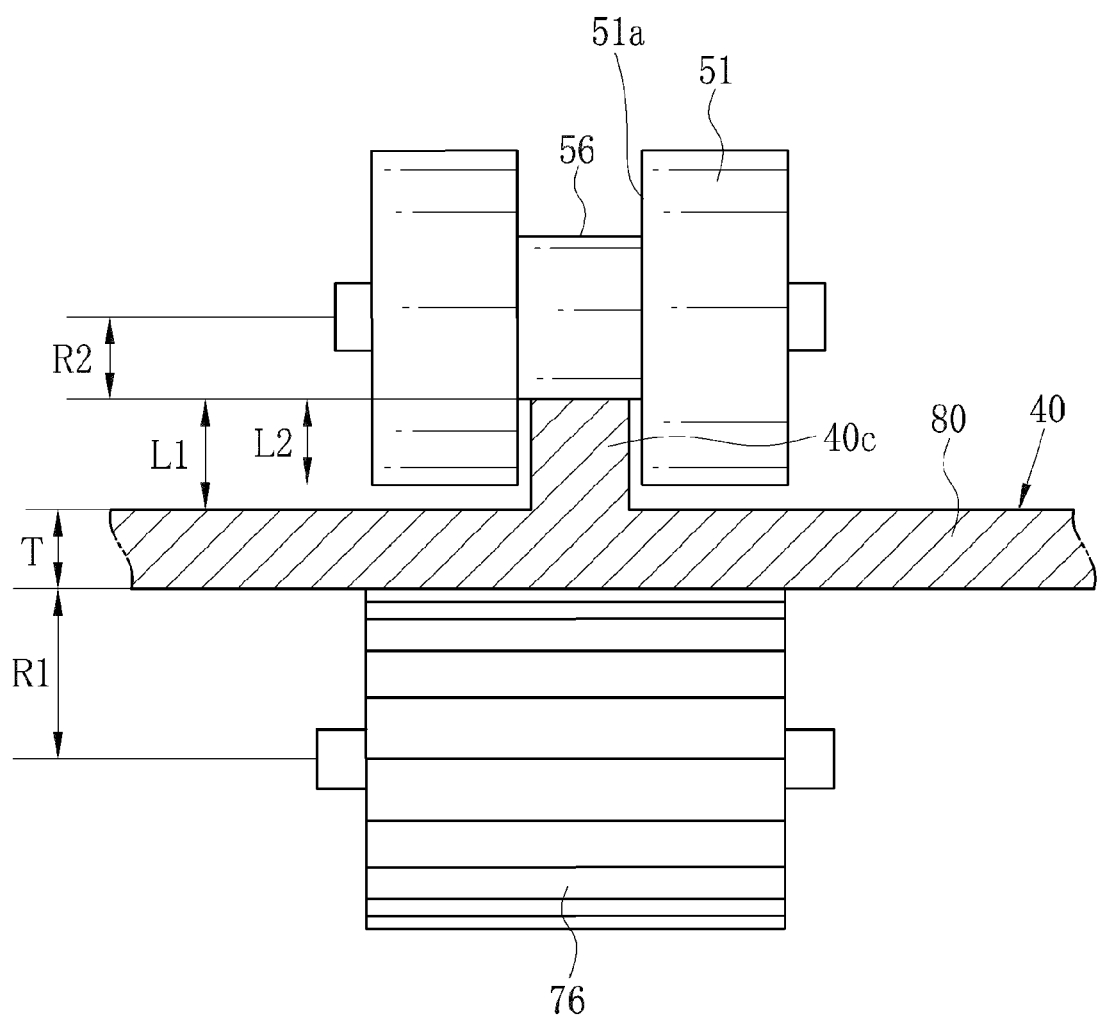
FIG. 8 is a section in enlargement illustrating a state of placement of the rollers on the circulation device.

As illustrated in FIG. 8, the height L1 of the alignment projections 40c and the depth L2 of the location offset prevention grooves 51a-53a satisfy L1>L2. The location offset prevention groove 51a has a groove bottom surface 56. Only placement of the first roller 51 on the circulation device 40 causes the vertex of the alignment projection 40c to contact the groove bottom surface 56, but does not cause portions of the circulation device 40 without forming the alignment projections 40c to contact the first roller 51.

Figure 9:
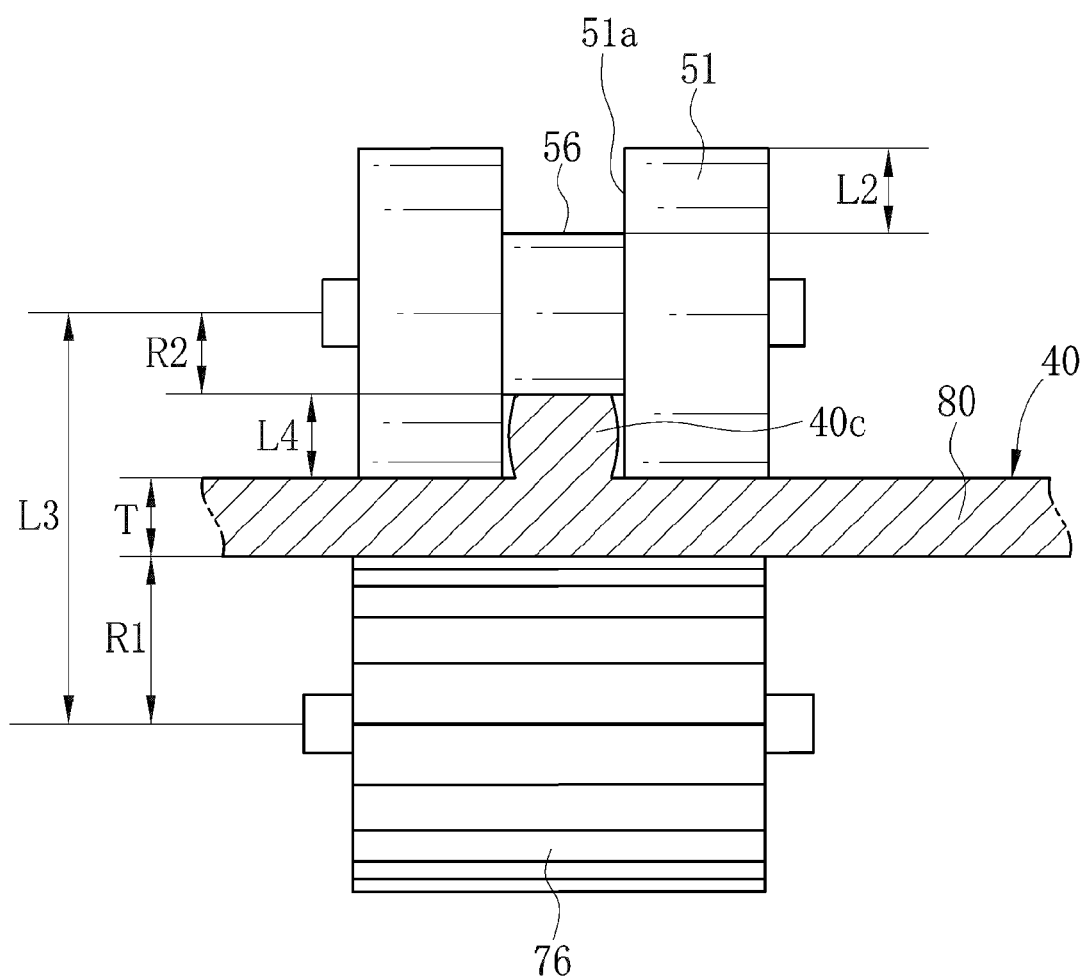
FIG. 9 is a section in enlargement illustrating the rollers on line IX-IX in FIG. 4.

As illustrated in FIG. 9, the first roller 51 is pressed and set to a securing position of tensioning the circulation device 40 between the first roller 51 and the drive wheels 76. Let L3 be an axis-to-axis distance between the first roller 51 and a distal one of the drive wheels 76. Let R1 be a radius of the drive wheels 76. Let R2 be a radius of the groove bottom surface 56 of the location offset prevention groove 51a of the first roller 51. Let T be a thickness of the circulation device 40. Then a condition T+L2+R1+R2>L3 is satisfied. Thus, the circulation device 40 is pressed on the outer surface of the first roller 51 in a state of small deformation of a portion of the circulation device 40 where the alignment projections 40c is not formed. In addition to the condition of the above formula, the height L1 of the alignment projections 40c and the depth L2 of the location offset prevention grooves 51a-53a satisfy L1>L2. A vertex of the alignment projections 40c is pressed on the groove bottom surface 56 in a state of deformation of the alignment projections 40c. A groove width of the location offset prevention groove 51a is larger than a width of the alignment projections 40c after the deformation.

The alignment projection 40c in FIG. 9 is in the deformed state. Let L4 be a height of the alignment projection 40c after the deformation. A condition L4=L2<L1 (initial height of the alignment projection 40c before the deformation) is satisfied, to satisfy the condition T+L4+R1+R2>L3. In combination with a proximal one of the drive wheels 76 adjacent to the rollers 52 and 53, the condition of this formula is satisfied.

The distal guide ring 67 includes an annular ridge 67a and a guide flange 67b, the annular ridge 67a being received in an opening 63c, the guide flange 67b preventing a tissue wall of the gastrointestinal tract from entry to the inside of the assist assembly 20. The guide flange 67b is inclined conically, of which an outer form is substantially triangular similarly to an inner surface of the support sleeve 42. The proximal guide ring 68 is constructed similarly to the distal guide ring 67, and includes a guide flange 68b and an annular ridge 68a received in an opening 66a of the support frame 66.

The support frame 66 is in the same shape (substantially triangular) as the container sleeve 63, and has the opening 66a which communicates with a receiving channel 61a (entry hole) of the attachment sleeve 61. Also, a cutout 66b is formed in the support frame 66 for containing the input gear 74 rotatably. The input gear 74 in the cutout 66b is meshed with the spur gear 72 of the drive sleeve 62. The torque wire 22 is connected with the input gear 74 through holes (see FIG. 4) formed in respectively the proximal guide ring 68 and the support frame 66.

The operation of the assist assembly 20 is described next. At first, the tip device 3*a* of the endoscope 2 is mounted in the receiving channel 61*a* of the attachment sleeve 61 to fasten the assist assembly 20 on the tip device 3*a*. After mounting the tip device 3*a* on the assist assembly 20, a power source for the processing apparatus, the light source apparatus, the input interface 32 and the like is turned on. Then the tip device 3*a* of the endoscope 2 is entered in a gastrointestinal tract of a patient, for example, large intestine.

After the tip device 3*a* comes in to a predetermined position in the large intestine, for example, short of a sigmoid colon, the speed determining button 34 of the input interface 32 is operated, to determine a moving speed of the assist assembly 20. Then the drive control button 33 is operated to instruct advance (entry). The control device 31 rotates the motor 21 at a rotational speed according to the determined moving speed. The motor 21 rotates the input gear 74 by use of the torque wire 22. The input gear 74 causes the spur gear 72 to rotate the drive sleeve 62.

As the drive sleeve 62 rotates, the drive wheels 76 in mesh with the worm gear 71 of the drive sleeve 62 are rotated. The drive wheels 76, which support the circulation device 40 between the same and the first to third rollers 51-53, cause the circulation device 40 to turn (move) in the direction indicated by the arrow in FIG. 4. Outside the support sleeve 42, an operative run 78 of the circulation device 40 in contact with a tissue wall of the gastrointestinal tract moves in the proximal direction. In contrast, a return run 80 of the circulation device 40 disposed inside the support sleeve 42 moves in a distal direction. The circulation device 40 contacting the tissue wall advances, as force for advance along the tissue wall is created with the tip device 3*a*.

The circulation device 40 is prevented from offsetting in the circumferential direction CD, as the alignment projections 40*c* of the circulation device 40 are entered in the location offset prevention grooves 51*a*-53*a* of the first to third rollers 51-53.

Also, the height L1 of the alignment projections 40*c* and the depth L2 of the location offset prevention grooves 51*a*-53*a* satisfy the condition L1>L2. The axis-to-axis distance L3 between the first to third rollers 51-53 and the drive wheels 76 adjacent thereto, the radius R1 of the drive wheels 76, the radius R2 of the groove bottom surface 56 of the location offset prevention grooves 51*a*-53*a* of the first to third rollers 51-53, and the thickness T of the circulation device 40 satisfy the condition T+L2+R1+R2>L3. As illustrated in FIG. 9, the vertex of the alignment projections 40*c* is pressed on the groove bottom surface 56 in their deformed state. The inner surface of the circulation device 40 is pressed on the outer surface of the first to third rollers 51-53. Accordingly, high driving force can be obtained, as pressure of contact between the alignment projections 40*c* and the location offset prevention grooves 51*a*-53*a* of the first to third rollers 51-53 and between the inner surface of the circulation device 40 and the outer surface of the first to third rollers 51-53 becomes higher than in a condition without contact of alignment projections with the groove bottom surface of the location offset prevention grooves or in a condition without contact of the inner surface of the circulation device with the rollers.

To change the speed, the speed determining button 34 of the input interface 32 is operated. Thus, a rotational speed of the motor 21 is changed. A speed of endless movement of the circulation device 40 is changed. When the return is instructed by operating the drive control button 33 of the input interface 32, the motor 21 is rotated backwards. A backward rotation of the motor 21 is transmitted by the torque wire 22 to the circulation device 40, to move the tip device 3*a* in a proximal direction. Also, a command signal for stop is inputted. Rotation of the motor 21 is stopped to stop the movement of circulation of the circulation device 40. Those operating steps are carried out suitably, so it is possible to advance the tip device 3*a* of the endoscope 2 to a desired position in a large intestine.

Light from the light source apparatus is transmitted through the light guide device 18 and the lighting windows 8*a* and 8*b* and applied to the inside of the gastrointestinal tract. An object of imaging during the lighting is imaged by the CCD image sensor incorporated in the tip device 3*a*. An image signal from the CCD image sensor is sent by the signal cable 17 and the universal cord 5 to the processing apparatus. The processing apparatus processes the image signal for image processing. The image signal is sent to a monitor (not shown) as a video signal, so that its screen displays an object image.

An operator views the inside of the gastrointestinal tract with the monitor. If a lesion is discovered, a medical instrument suitable for diagnosis or treatment of the lesion is entered in the forceps inlet 13 and protruded from the forceps outlet 9, to treat the lesion or draw tissue.

The viewing window 7 may be polluted with body fluid and the like. To wash the viewing window 7, the fluid button 15 is operated to draw washing water from the air/water supply apparatus to the ejection nozzle 10 through the air/water supply tube 16. The washing water is ejected by the ejection nozzle 10 toward the viewing window 7, and eliminates the dirt stuck on the viewing window 7. Then air from the air/water supply apparatus is blown by the ejection nozzle 10 to the viewing window 7 to blow away the remainder of the washing liquid on the viewing window 7.

In the above embodiment, the height L1 of the alignment projections and the depth L2 of the location offset prevention grooves satisfy the condition L1>L2. However, it is possible that L1=L2. In short, a condition L1≥L2 can be satisfied according to the invention.

In the above embodiment, the alignment projections are continuous on the entire circumference of the circulation device. However, the alignment projections can be divided with intervals. In the above embodiment, the entry and removal of the endoscope are assisted by the forward and backward movement in the distal and proximal directions. However, only the forward movement in the distal direction may be carried out for the endoscope.

In the above embodiment, the outer surface of the support sleeve is circular. However, the outer surface may be polygonal, for example, triangular, quadrangular or the like. The positions of disposing the roller units 45 are not limited to three. The number of those is changeable suitably.

In the above embodiment, the first to third rollers 51-53 include three arranged in the axial direction AD. However, the number of idler rollers may be two, or four or more. In the above embodiment, the drive wheels 76 include two arranged in the axial direction AD. However, the number of the drive wheel may be one or more in the axial direction.

In the above embodiment, the circulation device 40 of the bag shape is used (endless track device). However, a circulation device may be a plurality of endless belts. The endless belts are disposed about the support sleeve 42 with a suitable interval. In the above embodiment, the drive wheels are used as a drive mechanism. However, the worm gear 71 may directly drive the circulation device or endless belts, and no drive wheel may be used. A turning direction of the endless belts is opposite to that of the circulation device 40. It is necessary to change a relationship between a command signal of the forward and backward movement with the input interface 32 and a rotational direction of the motor 21.

The present invention is applied to the medical endoscope in the above embodiment. However, it is possible to apply the present invention in an industrial endoscope apparatus, probe apparatus or the like.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assist assembly for propulsion of a tip device of an endoscope in a body cavity, comprising:
   an attachment sleeve for mounting on said tip device;
   a support sleeve disposed around said attachment sleeve;
   a deformable circulation device, disposed to extend over inner and outer surfaces of said support sleeve, for contacting a wall of said body cavity, and endlessly moving in an axial direction of said tip device;
   plural rollers, disposed on said support sleeve in a rotatable manner, for pressing an inner surface of said circulation device;
   a projection formed on said inner surface of said circulation device to project at a height L1;
   a location offset prevention groove, formed in said rollers at a depth L2, for receiving said projection, and satisfying a condition:

L1>L2 so as to press said projection in a radial direction of said rollers, to prevent location offset of said circulation device from said rollers; and
   a drive mechanism for tensioning said circulation device in cooperation with said rollers by deforming said projection in said location offset prevention groove and by pressing said inner surface of said circulation device on said rollers, endlessly to drive said circulation device by rotating.

2. An assist assembly as defined in claim 1, wherein said projection continuously extends in said axial direction on said circulation device.

3. An assist assembly as defined in claim 1, further comprising an insertion groove, formed in said support sleeve, for receiving insertion of said projection.

4. An assist assembly as defined in claim 3, wherein said plural rollers are arranged in said axial direction.

5. An assist assembly as defined in claim 3, wherein said rollers are first to Nth rollers arranged on said support sleeve at a predetermined pitch in a circumferential direction defined around said axial direction;
   said projection is first to Nth projections arranged on said circulation device to correspond to respectively said first to Nth rollers.

6. An assist assembly as defined in claim 3, wherein said drive mechanism includes:
   a drive sleeve disposed between said attachment sleeve and said support sleeve;
   a worm gear, formed on an outer surface of said drive sleeve, for moving said circulation device.

7. An assist assembly as defined in claim 6, wherein said drive mechanism includes a plurality of rotatable drive wheels, engaged with said worm gear and said circulation device, for moving said circulation device upon rotation of said worm gear.

8. An assist assembly as defined in claim 3, wherein said circulation device covers said support sleeve in an entire manner in a bag shape.

9. An assist assembly as defined in claim 3, wherein said circulation device includes plural endless belts for partially covering said support sleeve in a circumferential direction.

10. The assist assembly as defined in claim 1, wherein a width of said location offset prevention groove is larger than a width of the deformed projection.

11. The assist assembly as defined in claim 1, wherein a vertex of the deformed projection is pressed onto a bottom surface of said location offset prevention groove.

* * * * *